US011227692B2

(12) United States Patent
Rumbell et al.

(10) Patent No.: US 11,227,692 B2
(45) Date of Patent: Jan. 18, 2022

(54) NEURON MODEL SIMULATION

(71) Applicant: INTERNATIONAL BUSINESS MACHINES CORPORATION, Armonk, NY (US)

(72) Inventors: Tim Rumbell, New York, NY (US); James R. Kozloski, New Fairfield, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 738 days.

(21) Appl. No.: 15/856,582

(22) Filed: Dec. 28, 2017

(65) Prior Publication Data
US 2019/0206573 A1 Jul. 4, 2019

(51) Int. Cl.
*G16H 50/80* (2018.01)
*G16B 20/00* (2019.01)
*G16B 40/20* (2019.01)
*G16H 50/50* (2018.01)
*G06N 3/02* (2006.01)
*G16H 20/10* (2018.01)

(52) U.S. Cl.
CPC .............. *G16H 50/80* (2018.01); *G06N 3/02* (2013.01); *G16B 20/00* (2019.02); *G16B 40/20* (2019.02); *G16H 20/10* (2018.01); *G16H 50/50* (2018.01)

(58) Field of Classification Search
CPC combination set(s) only.
See application file for complete search history.

(56) References Cited

U.S. PATENT DOCUMENTS 5,121,231 A * 6/1992 Jenkins et al.
5,849,995 A  12/1998 Hayden et al.
(Continued)

OTHER PUBLICATIONS

Bank et al., "Pharmacogenetic biomarkers for predicting drug response," Expert Review Of Molecular Diagnostics, vol. 14, No. 6, 2014, pp. 1-13.
(Continued)

*Primary Examiner* — Michael Tomaszewski
*Assistant Examiner* — William T. Monticello
(74) *Attorney, Agent, or Firm* — Cantor Colburn LLP; Kristofer Haggerty

(57) ABSTRACT

One or more embodiments of the present invention include a computer-implemented method for generating neuronal models for personalized drug treatment selection for a patient. The method includes receiving allelic information for at least one neurophysiological coding region of a genome of the patient, and a physiological model of a disease associated with the genome. The method further includes determining a set of ion channels correlated with the allelic information, and receiving a set of phenotypic measurement ranges associated with the ion channels from the determined set. The method further includes performing a simulation to generate multiple neuronal models comprising the set of ion channels with parameter values within the corresponding phenotypic measurement ranges, and analyzing the generated neuronal models to identify components that affect the physiological model. The method further includes selecting a drug for the patient based at least in part on the identified components.

20 Claims, 5 Drawing Sheets

(56) References Cited

U.S. PATENT DOCUMENTS

| | | |
|---|---|---|
| 6,629,935 B1 | 10/2003 | Miller et al. |
| 7,461,006 B2 | 12/2008 | Gogolak |
| 7,945,392 B2 | 5/2011 | Siekmeier et al. |
| 8,150,629 B2 | 4/2012 | Geerts et al. |
| 8,589,175 B2 | 11/2013 | Glauser et al. |
| 8,688,385 B2 | 4/2014 | Mrazek et al. |
| 2004/0241720 A1* | 12/2004 | Salkoff et al. |
| 2006/0136140 A1* | 6/2006 | Perschke et al. |
| 2008/0038730 A1* | 2/2008 | Von der Kammer et al. |
| 2009/0306534 A1* | 12/2009 | Pizzagalli et al. |
| 2013/0262155 A1 | 10/2013 | Hinkamp |
| 2014/0336479 A1* | 11/2014 | Ando et al. |
| 2014/0358513 A1* | 12/2014 | Kaplan et al. |
| 2017/0027636 A1* | 2/2017 | Whayne et al. |
| 2018/0271453 A1* | 9/2018 | Pak et al. |
| 2018/0330824 A1* | 11/2018 | Athey et al. |
| 2018/0368720 A1* | 12/2018 | Lee et al. |
| 2019/0175916 A1* | 6/2019 | Grill et al. |

OTHER PUBLICATIONS

Pourkavoos, "Unique risks, benefits, and challenges of developing drug-drug combination products in a pharmaceutical industrial setting," Combination Products in Therapy 2, vol. 1, No. 2, 2012, pp. 1-31.

Tonk et al., "Assessment of pharmacogenetic tests: presenting measures of clinical validity and potential population impact in association studies," The Pharmacogenomics Journal, vol. 17, 2017, pp. 1-7.

Min et al., "Prediction of drug-drug interaction potential using physiologically based pharmacokinetic modeling," Archives of Pharmacal Research, 2017, 24 pages.

\* cited by examiner

NEURON MODEL SIMULATION

BACKGROUND

The present invention relates in general to computer simulations. More specifically, the present invention relates to predicting drug effects on a neurophysiological trait in a patient given patient genotype information using neuro-model simulation(s) and determining therapeutic decision/strategy specifically for the patient.

Neurophysiological traits are features of neural activity that usually occupy a particular range for a healthy individual, but can occupy another range in a disease state. For example, the firing rate of a specific neuron type within a brain region can be at a certain rate for a healthy individual, but a hallmark of a disease can be an elevated firing rate for that neuron type in that brain region. It is desirable to select a drug that targets the most reliable way for that trait to be brought back into the healthy range.

SUMMARY

One or more embodiments of the present invention include a computer-implemented method for generating neuronal models for personalized drug treatment selection for a patient. The method includes receiving allelic information for at least one neurophysiological coding region of a genome of the patient. The method further includes receiving a physiological model of a disease associated with the genome of the patient. The method further includes determining, from an ion channel database, a set of ion channels correlated with the allelic information. The method further includes receiving a set of phenotypic measurement ranges, each phenotypic measurement range associated with a corresponding ion channel from the determined set of ion channels. The method further includes performing a simulation to generate multiple neuronal models comprising the set of ion channels with parameter values within the corresponding phenotypic measurement ranges. The method further includes analyzing the generated neuronal models to identify components that affect the physiological model. The method further includes selecting a drug for the patient based at least in part on the identified components.

One or more embodiments of the present invention includes a system for personalized drug treatment selection for a patient. The system includes a memory, and a processor communicatively coupled to the memory. The processor receives allelic information for at least one neurophysiological coding region of a genome of the patient. The processor further receives a physiological model of a disease associated with the genome of the patient. The processor further determines, from an ion channel database, a set of ion channels correlated with the allelic information. The processor further receives a set of phenotypic measurement ranges, each phenotypic measurement range associated with a corresponding ion channel from the determined set of ion channels. The processor further performs a simulation to generate multiple neuronal models comprising the set of ion channels with parameter values within the corresponding phenotypic measurement ranges. The processor further analyzes the generated neuronal models to identify components that affect the physiological model. The processor further selects a drug for the patient based at least in part on the identified components.

One or more embodiments of the present invention include computer program product including a computer storage device having computer readable instructions stored therein, where the computer readable instructions are executable by a processing unit for generating neuronal models for personalized drug treatment selection for a patient. The selection includes receiving allelic information for at least one neurophysiological coding region of a genome of the patient. The selection further includes receiving a physiological model of a disease associated with the genome of the patient. The selection further includes determining, from an ion channel database, a set of ion channels correlated with the allelic information. The selection further includes receiving a set of phenotypic measurement ranges, each phenotypic measurement range associated with a corresponding ion channel from the determined set of ion channels. The selection further includes performing a simulation to generate multiple neuronal models comprising the set of ion channels with parameter values within the corresponding phenotypic measurement ranges. The selection further includes analyzing the generated neuronal models to identify components that affect the physiological model. The selection further includes selecting a drug for the patient based at least in part on the identified components.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The examples described throughout the present document will be better understood with reference to the following drawings and description. The components in the figures are not necessarily to scale. Moreover, in the figures, like-referenced numerals designate corresponding parts throughout the different views.

Figure 1:
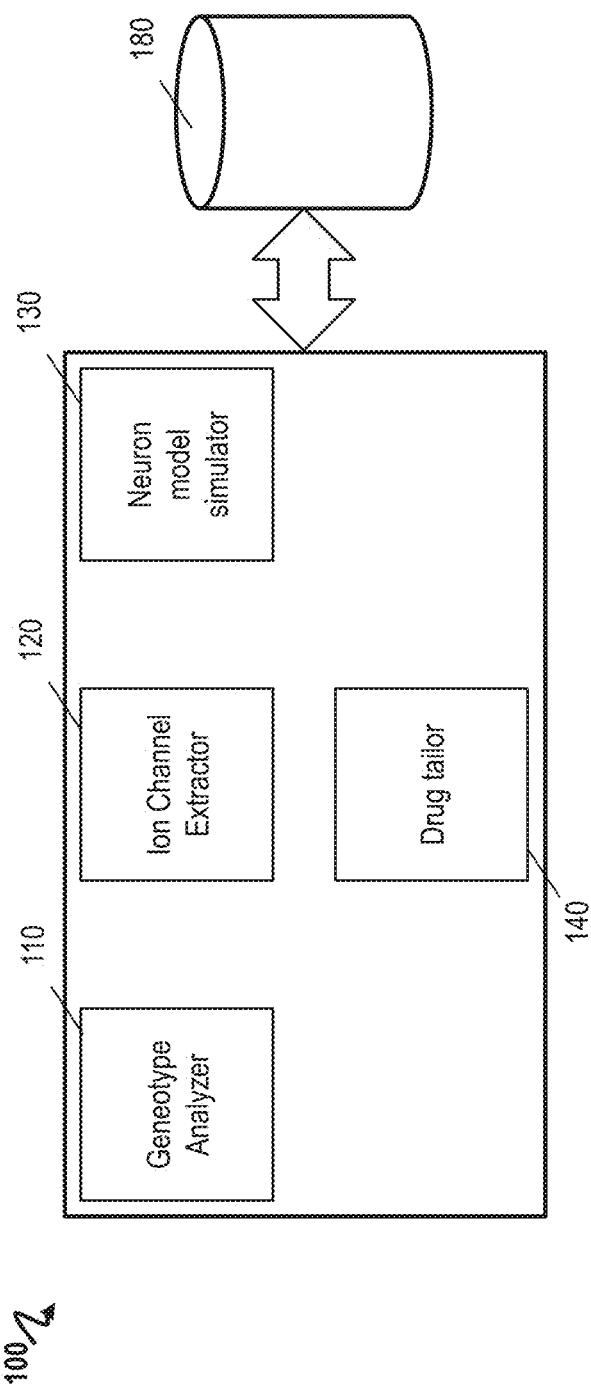
FIG. 1 depicts an example neuron model system according to one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In neuroscience, a "neuron" is a cell that is capable of processing information, via an active membrane that can generate and conduct electrical signals. Points of contact between neurons at which information is exchanged are called synapses. With the help of ion pumps in the membrane, a concentration gradient is established. This concentration gradient acts as an energy reservoir which is used to establish and maintain a potential difference between the two sides of the membrane. Scattered throughout the membrane are ion channels, which may be, for example, aqueous pores formed by transmembrane proteins, which facilitate the transport of ions over the membrane.

There are many different types of ion channels. The basic function of the ion channels is to facilitate the diffusion of ions through the membrane of neurons. A commonality between all ion channels is that they allow for a high rate, up to $10^6$ ions per second, of transfer through the cell membrane. This flow of ions creates electrical current on the order of $10^{-12}$ to $10^{-10}$ amperes per channel. Such currents are large enough to produce rapid changes in the membrane potential, and the electrical potential difference between the cell interior and exterior. Because calcium and sodium ions are at higher concentration extracellularly than intracellularly, openings of calcium and sodium channels cause these cations to enter the cell and depolarize the membrane potential. For analogous reasons, when potassium leaves or chloride enters the cell through open channels, the cell interior becomes more negative, or hyperpolarized. However, not all ions can pass through a given ion channel. One of the reasons for this is that most ion channels have a selective permeability to different ions. The Hodgkin-Huxley model, which is the de facto standard in modeling ionic currents puts forth the notion that the gates may be, for example, controlled by voltage-sensitive particles.

Most ion channels are gated i.e. capable of making transitions between conducting and non-conducting conformations. Channel gating can be induced by extracellular ligands, intracellular second messengers and metabolites, protein-protein interactions, phosphorylation, and other factors. In addition, many ion channels are gated by another regulatory signal—the membrane potential itself. Voltage-gated ion channels respond to and modify the changes in membrane potential produced by the binding of neurotransmitters to ligand-gated ion channels at synapses.

Mutations of key channel molecules can cause human neuromuscular disorders. Distinct clinical syndromes or traits are observed in many cases based on the specific alterations the mutations produce in channel activity. For example, reducing the activity of potassium channels in the nerve fiber delays action potential repolarization and lowers the amount of excitation needed to produce action potentials. Potassium channel mutations with these effects underlie hereditary forms of myokymia, a spontaneous, involuntary rippling movement of skeletal muscle based on abnormal spontaneous action potential generation within the peripheral nerve. A large number of different mutations in genes encoding subunits of the acetylcholine receptor cause congenital myesthenic syndromes, disorders associated with muscle weakness and fatigue.

Further, epileptic seizures are behavioral attacks resulting from the overly synchronized and excessive activity of large groups of brain neurons. Symptoms vary widely, depending on the region and extent of the brain that participates in the abnormal electrical activity, but can include alterations or loss of consciousness, sustained or rhythmic muscle contraction, stereotyped gestural movements, and visual or somatosensory hallucinations.

As described earlier, neurophysiological traits are features of neural activity that usually occupy a particular range for a healthy individual, but can occupy another range in a disease state. For example, the firing rate of a specific neuron type within a brain region can be at a certain rate for a healthy individual, but a hallmark of a disease can be an elevated firing rate for that neuron type in that brain region. It is desirable to select a drug that targets the most reliable way for that trait to be brought back into the healthy range.

Such neurophysiological traits are not identical in all single units (e.g. individual neuron, or small microcircuit—building blocks of brain activity) within an individual's brain. For example, every neuron of a particular cell type in a particular brain region has a different value for that trait (e.g. different firing rate) depending on the neuron's unique context and environment.

For any trait, there are several ways of modulating the trait by altering properties of a neuron. Changes to various combinations of ion channel properties can modulate the trait in a particular direction for any single unit. However, the most effective way of modulating the trait can be different for each single unit. Understanding the most parsimonious way of modulating the trait across the population of unique single units facilitates selecting/tailoring an effective drug for the patient to adjust the modulation to a healthy range. The one or more embodiments of the present invention address such technical challenges by performing neuron model simulation(s) to identify the modulating of the trait.

Further, single unit properties are variable across the population of unique single units, but have a common source in that they all derive initially from the genotype of the individual. For example, a neuron of a particular type will require a certain complement of ion channels to function broadly as a member of that class of neuron, filling an appropriate role in the brain. For example, types of neurons can include sensory neurons, motor neurons, and interneurons. It should be noted that the classifications of neurons can be different in different embodiments. Gene expression controls how these ion channels get constructed and inserted into the cell membrane. However, the precise expression of particular genes regulates this complement of ion channels differently between individuals, thereby regulating a particular cell type differently.

Differences in genotype can be represented as differences in possible parameter values that the components of a single unit model can take. For example, a unique neuron of a particular cell type can match the stereotypical behavior required of that cell type to perform its functional role in a variety of ways by using a variety of ion channel combinations. The particular parameter combinations that are to be used to regulate a single unit within the functionally viable range for a given genotype can be differentially affected by perturbations aiming to alter the neurophysiological traits of that genotype. Hence, establishing the parameter combinations that are accessible within a given set of parameter ranges (genotype) can facilitate determining healthy trait values. The embodiments of the present invention address such technical challenges and facilitate establishing the parameter combinations to identify the health trait values.

The embodiments of the present invention use an evolutionary algorithm combined with a soft thresholding of error values combined with a penalty term for crowdedness within trait-space to establish which parameter combinations are capable of generating the "healthy" range for a trait, given a particular genotype. The described embodiments improve the efficiency, which results in improved speed determining and/or tailoring a drug to be given to a patient. Efficiency is derived from the evolutionary algorithm (described further) for simulating neuron models, which is a more efficient parameter search than a grid search that is typically used. The parameter search further improves efficiency of tailoring a drug for a specific patient by providing a database of model parameter sets to analyze for optimal control of the range of traits. The algorithm thereby improves efficiency over other tailoring methods based on responses to certain medications, trial and error, or machine learning over the gene/expression data aimed at predicting drug efficacy directly from gene information. Further yet, the described embodiments of the invention improve reliability of the determining the parameter combinations for generating the "healthy" range for a trait. Reliability is derived from the ability to modulate multiple ion channels simultaneously in the simulation along optimal axes of control, and thereby allowing more control over a trait.

Further yet, the embodiments of the present invention use statistical modeling techniques, such as partial least square regression (PLSR), to regress parameter sets against the identified trait values generated by the model with that parameter set. Embodiments of the invention accordingly facilitate identification of functional regulatory units that specify particular ion channel parameter combinations that, if perturbed, parsimoniously alters the desired trait value across the most single units of the genotype.

The channel disorders of the neuromuscular synapse illustrate how a large variety of disease phenotypes can result from mutations in channels functioning together at a single anatomical site. In the brain, a far greater variety of channels are expressed, and the roles played by specific channels are, for the most part, poorly understood. The embodiments of the present invention facilitate analyzing the contributions made by a large number of the channel genes at the cellular and neuronal network level. Further, embodiments of the present invention facilitates identifying compounds that modify the activity of individual channel types with greater specificity.

For example, the embodiments of the present invention can be used for diagnosis for a particular mood disorder (a binocular switching task). Information about task performance, along with genetic factors, can then be used to predict drug effect and determine drug dosing, with the underlying assumptions of the theoretical model of bipolar disorder described. Thus, embodiments of the present invention facilitates using patient data (genotype) combined with an unbiased approach to parameterize a simulation that automatically generates a therapeutic target. The embodiments of the present invention do so by modelling and simulation of a system involved in the disease, and the parameters required to modulate the system back into a particular target range. The genotypic information is used to restrict ranges of particular parameters within the simulation, and the drug/dosage is selected based on the simulations result identifying the targets in terms of neurophysiological properties such as proteins or neurotransmitters that are most likely to restore the simulated dysfunctional to a normal state. Therefore, the embodiments of the present invention, rather than relying directly on the genetic information directly to search for drugs, use the genetic information to generate and constrain a computational model/ simulation of neuronal models of the patient, and then analyze the neuronal models to determine the drug targets.

FIG. 1 depicts an example neuron model system according to one or more embodiments of the present invention. The system 100 includes a genotype analyzer 110, an ion channel extractor 120, a neuron model simulator 130, a drug tailor 140, and a data repository 180, among other components. The data repository 180 includes one or more databases, such as an ion channel database, a drug efficacy database and the like. The one or more components of the system 100 communicate with the data repository through a communication network, in a wired and/or wireless manner.

The system 100 receives as input, a genotype of an individual, for example a patient for whom a drug is to be selected/tailored. The genotype analyzer 110 analyzes the input and extracts gene expression estimates relating to the set of neuronal cell membrane proteins that define a particular single unit model for the patient. The gene expression estimates provide ranges for parameters to generate a neuron model for the patient.

The term "genotype" refers to the alleles present in genomic DNA from the patient where an allele can be defined by the particular nucleotide(s) present in a nucleic acid sequence at a particular sites(s). A "genotype" is the nucleotide(s) present at a single polymorphic site known to vary in the human population. The "genotype information" received as input is intended information pertaining to variances or alterations in the genetic structure of a gene or locus of interest. Genotype information can indicate the presence or absence of a predetermined allele. Further, a "loci of interest" can be a gene, allele, or polymorphism of interest. Genes or loci of interest include genes that encode a) medication specific metabolizing enzymes, b) medication specific transporters, c) medication specific receptors, d) enzymes, transporters or receptors affecting other drugs that interact with the medication in question or e) body functions that affect that activities of the medication in question.

Further, the system 100 receives, as input, the disease-related traits that represent therapeutic targets of interest for the patient. Examples of disease-related traits that represent therapeutic targets of interest for the patient include the rheobase of projection neurons of the striatum, this trait being lower in Huntington's disease than in healthy controls; another is the level of dopamine neuron firing rates in Parkinson's disease, this trait requiring elevation to compensate for dopamine neuron loss; another is the burst firing/single spike firing modes of dopamine neurons, this trait requiring modulation in schizophrenia. It should be noted that the above are some examples of the various possible disease traits that may be received by the system 100. Using the estimated parameter ranges determined from the individual's genotype, the ion channel extractor 120 searches an ion channel database for ion channels that fall within 'healthy' ranges of the traits of interest. In one or more examples, the ion channel extractor 120 performs the search using an evolutionary algorithm with a combination of soft-thresholding of error values and crowdedness penalty in the trait-space. "Soft-thresholding" here refers to an error cutoff such that any ion channel parameters, which are identified as producing 'acceptable' trait values within the "healthy" range of trait values for that trait, are considered equally viable, and so are all given an error value of zero. The crowdedness penalty then biases the evolutionary search towards less crowded regions of trait-space, facilitating a uniform sampling of the "healthy" trait values.

The neuron model simulator 130 further analyzes the ion channels that are identified to be in the "healthy" trait-space. In one or more examples, the neuron model simulator 130 uses partial least squares regression (PLSR), a 2-gate hyperplane normal algorithm, or any other such algorithm for regressing trait values against parameter combinations from the identified ion channels. For example, PLSR is a statistical algorithm similar to principal component regression that combines features from principal component analysis (PCA) and multiple linear regression (MLR). PLSR facilitates finding a linear regression model that predicts a set of dependent variables (DV) from a set of independent variables (IV). This is achieved by projecting the IV and DV to new latent variables spaces that have the optimal predictive power. Latent variables, unlike observable variables such as ion channel conductance, are variables that are not observed but are instead inferred from other observables.

In another example, a 2-gate hyperplane normal algorithm is used. Here at least two ranges of traits (i.e., "gates") are searched by the optimization, identifying parameter sets that bear the label of the gate. For example, one gate may bear the label "wild-type" while the other may bear the label "disease-type." Next, by inserting a hyperplane into the parameter space, which minimizes loss of categorizing a parameter set as from one label or the other, the system 100 represents the movement through parameter space necessary to transform a neuron trait from "wild-type" to "disease-type" as the vector normal to the hyperplane. The hyperplane is determined such that the hyperplane categorizes parameter sets based on the gate for which they were optimized and a normal to the hyperplane is pointing in the direction of parameter sets derived from one of the gates, for example, the "wild-type." In one or more examples, the hyperplane is determined using techniques such as the perceptron algorithm if the two (or more) gates are linearly separable. Alternatively, or in addition, if the two gates are not linearly separable, multiple perceptron may be used. Alternatively, or in addition, in one or more examples, support vector machine algorithm can be used to determine the hyperplane. The hyperplane determination algorithms can be implemented using an artificial neural network in one or more examples.

The neuron model simulator accordingly identifies a set of regression coefficients or normal vector coefficients with one normalized coefficient for each parameter in the system that explain a maximal amount of variation within trait-space. The neuron model simulator 130 outputs the set of regression coefficients, which represent a specific combination of parameters that can alter a trait value within the targeted single unit.

The system 100 accordingly facilitates predicting that a therapeutic intervention targeting precisely the parameters represented by the regression coefficients, in the specific ratio shown by the ratio of the coefficients, can have maximal likelihood of altering traits in a desired direction in the patient. It should be noted that the prediction is individualized, that is the prediction can be different for different patients.

The drug tailor 140 determines a drug or a combination of drugs that performs the manipulation of the parameters based on the patient's genotype. For example, a drug database that contains information about several drugs and each drug's efficacy to affect one or more neuromorphic or channel-specific traits is searched by the drug tailor 140 to identify the one or more drugs to be used that affect the identified parameters of the ion channels.

Alternatively, or in addition, the drug tailor 140 predicts effects of a particular therapeutic drug/combination on alternate traits, predicting side effects of a treatment in terms of the treatment modifying alternative single unit behaviors that were not targeted by the therapeutic design process.

Figure 2:
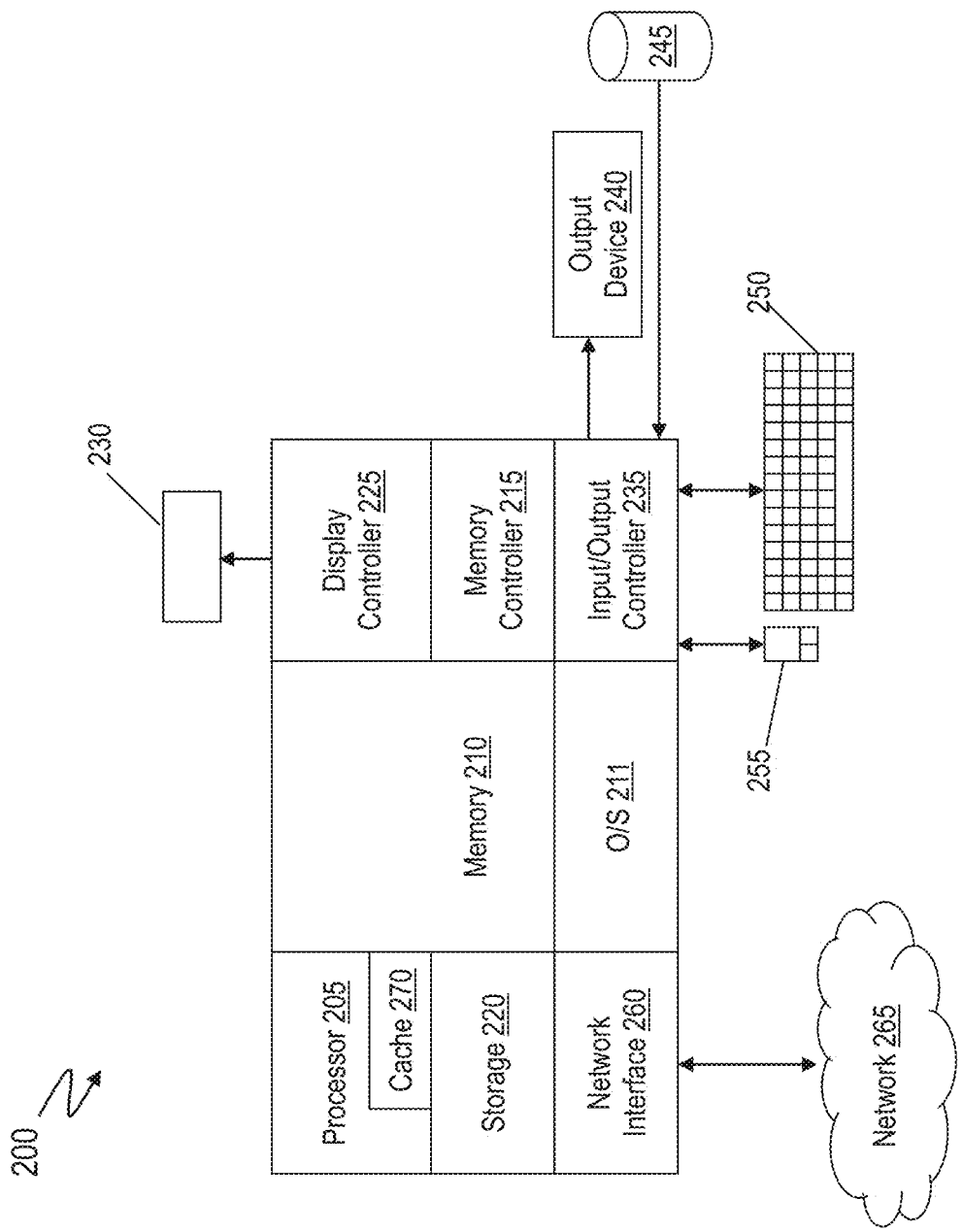
FIG. 2 illustrates an example system according to one or more embodiments of the present invention.

FIG. 2 illustrates an example system 200 according to one or more embodiments of the present invention. The system 200 can be a communication apparatus, such as a computer. For example, the system 200 can be a desktop computer, a tablet computer, a laptop computer, a phone, such as a smartphone, a server computer, or any other device that communicates via a network 265. The system 200 includes hardware, such as electronic circuitry. In one or more examples, the system 100, and/or each component of the system 100 can be represented by the system 200.

The system 200 includes, among other components, a processor 205, memory 210 coupled to a memory controller 215, and one or more input devices 245 and/or output devices 240, such as peripheral or control devices that are communicatively coupled via a local I/O controller 235. These devices 240 and 245 can include, for example, battery sensors, position sensors (altimeter, accelerometer, GPS), indicator/identification lights and the like. Input devices such as a conventional keyboard 250 and mouse 255 can be coupled to the I/O controller 235. The I/O controller 235 can be, for example, one or more buses or other wired or wireless connections, as are known in the art. The I/O controller 235 can have additional elements, which are omitted for simplicity, such as controllers, buffers (caches), drivers, repeaters, and receivers, to enable communications.

The I/O devices 240, 245 can further include devices that communicate both inputs and outputs, for instance disk and tape storage, a network interface card (MC) or modulator/demodulator (for accessing other files, devices, systems, or a network), a radio frequency (RF) or other transceiver, a telephonic interface, a bridge, a router, and the like.

The processor 205 is a hardware device for executing hardware instructions or software, particularly those stored in memory 210. The processor 205 can be a custom made or commercially available processor, a central processing unit (CPU), an auxiliary processor among several processors associated with the system 200, a semiconductor based microprocessor (in the form of a microchip or chip set), a macroprocessor, or other device for executing instructions. The processor 205 includes a cache 270, which can include, but is not limited to, an instruction cache to speed up executable instruction fetch, a data cache to speed up data fetch and store, and a translation lookaside buffer (TLB) used to speed up virtual-to-physical address translation for both executable instructions and data. The cache 270 can be organized as a hierarchy of more cache levels (L1, L2, and so on).

The memory 210 can include one or combinations of volatile memory elements (for example, random access memory, RAM, such as DRAM, SRAM, SDRAM) and nonvolatile memory elements (for example, ROM, erasable programmable read only memory (EPROM), electronically erasable programmable read only memory (EEPROM), programmable read only memory (PROM), tape, compact disc read only memory (CD-ROM), disk, diskette, cartridge, cassette or the like). Moreover, the memory 210 can incorporate electronic, magnetic, optical, or other types of storage media. Note that the memory 210 can have a distributed architecture, where various components are situated remote from one another but can be accessed by the processor 205.

The instructions in memory 210 can include one or more separate programs, each of which includes an ordered listing of executable instructions for implementing logical functions. In the example of FIG. 2, the instructions in the memory 210 include a suitable operating system (OS) 211. The operating system 211 essentially can control the execution of other computer programs and provides scheduling, input-output control, file and data management, memory management, and communication control and related services.

Additional data, including, for example, instructions for the processor 205 or other retrievable information, can be stored in storage 220, which can be a storage device such as a hard disk drive or solid state drive. The stored instructions in memory 210 or in storage 220 can include those enabling the processor to execute one or more aspects of the systems and methods described herein.

The system 200 can further include a display controller 225 coupled to a user interface or display 230. In some embodiments, the display 230 can be an LCD screen. In other embodiments, the display 230 can include a plurality of LED status lights. In some embodiments, the system 200 can further include a network interface 260 for coupling to a network 265. The network 265 can be an IP-based network for communication between the system 200 and an external server, client and the like via a broadband connection. In an embodiment, the network 265 can be a satellite network. The network 265 transmits and receives data between the system 200 and external systems. In some embodiments, the network 265 can be a managed IP network administered by a service provider. The network 265 can be implemented in a wireless fashion, for example, using wireless protocols and technologies, such as WiFi, WiMax, satellite, or any other. The network 265 can also be a packet-switched network such as a local area network, wide area network, metropolitan area network, the Internet, or other similar type of network environment. The network 265 can be a fixed wireless network, a wireless local area network (LAN), a wireless wide area network (WAN) a personal area network (PAN), a virtual private network (VPN), intranet or other suitable network system and can include equipment for receiving and transmitting signals.

Figure 3:
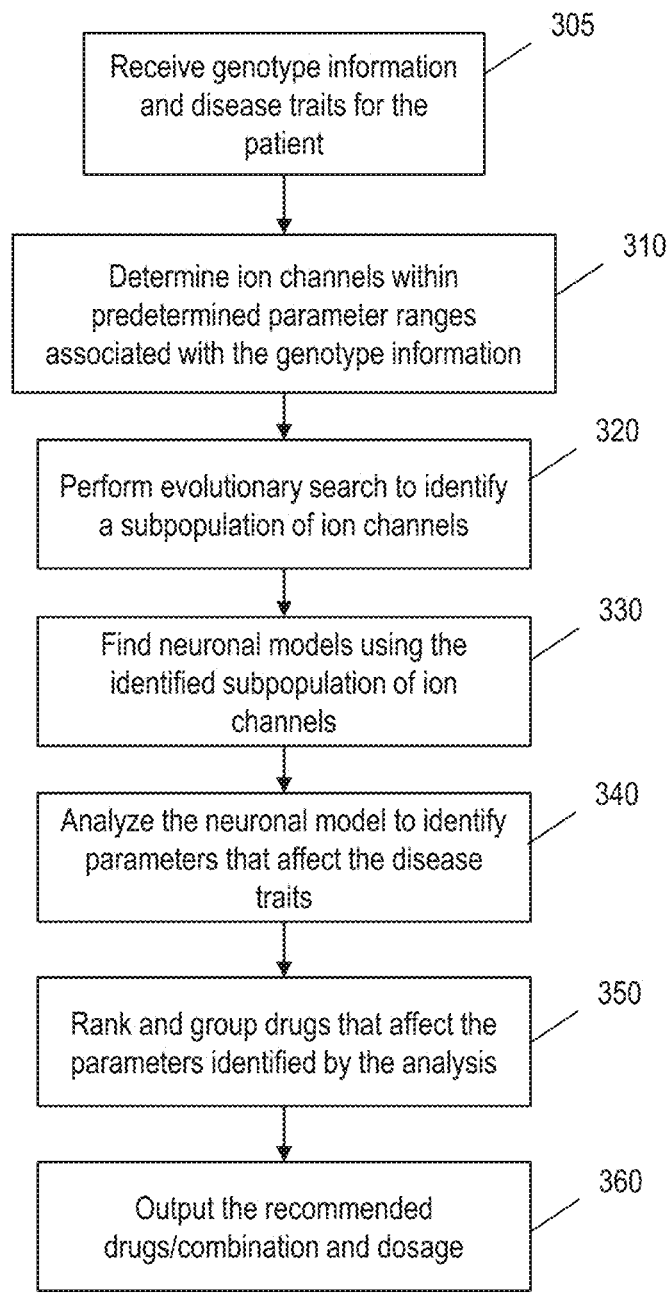
FIG. 3 illustrates a flowchart of an example method for selecting a drug combination for a patient according to one or more embodiments of the present invention.

FIG. 3 illustrates a flowchart of an example method for selecting a drug combination for a patient according to one or more embodiments of the present invention. The method includes receiving/accessing genotype information for at least one neurophysiologically relevant coding region of a patient genome, at 305. Examples include: ion channel subunit gene allelic information, receptor subunit gene allelic information, etc. The method further includes accessing a database of ion channel model parameter ranges correlated with the allelic information, at 310. The ion channel database is part of the data repository 180. Accessing the ion channel database includes determining a set of ion channels having a parameter within a predetermined measurement range. In one or more examples, two or more parameter measurement values can be used to select the set of ion channels, for example, oscillation frequency and amplitude.

The operation includes configuring one or more measurement ranges for a neuron model relevant to a phenotypic measure targeted by one or more drugs to be selected for the patient. For example, the phenotypic measure can be an oscillation frequency, oscillation amplitude, and the like for the neuron, which include the traits that are being analyzed. It should be noted that in one or more examples, multiple sets of measurement ranges can be used to create a "gate". The measurement ranges can be input by a user, in one or more examples.

The method further includes performing a population based evolutionary search with soft max crowdedness penalty, the search performed within the ion channels population that was identified in the phenotypic measurement space constrained by measurement ranges of the patient genotype, at 320. The resulting ion channels that are identified by the search are used to find neuronal models that generate phenotypic measures over patients' likely current and desired neuronal states, at 330. The one or more embodiments of the present invention thus use an evolutionary algorithm search for finding ion channel parameters in neuron models to generate a trait, and further applies a population-based search with soft-max thresholding to generate neuron models for drug tailoring. In one or more examples, the neuronal models are further configured as neural tissue models, and brain circuit models, with further optimization and phenotypic measures extracted from these composite models.

Figure 4:
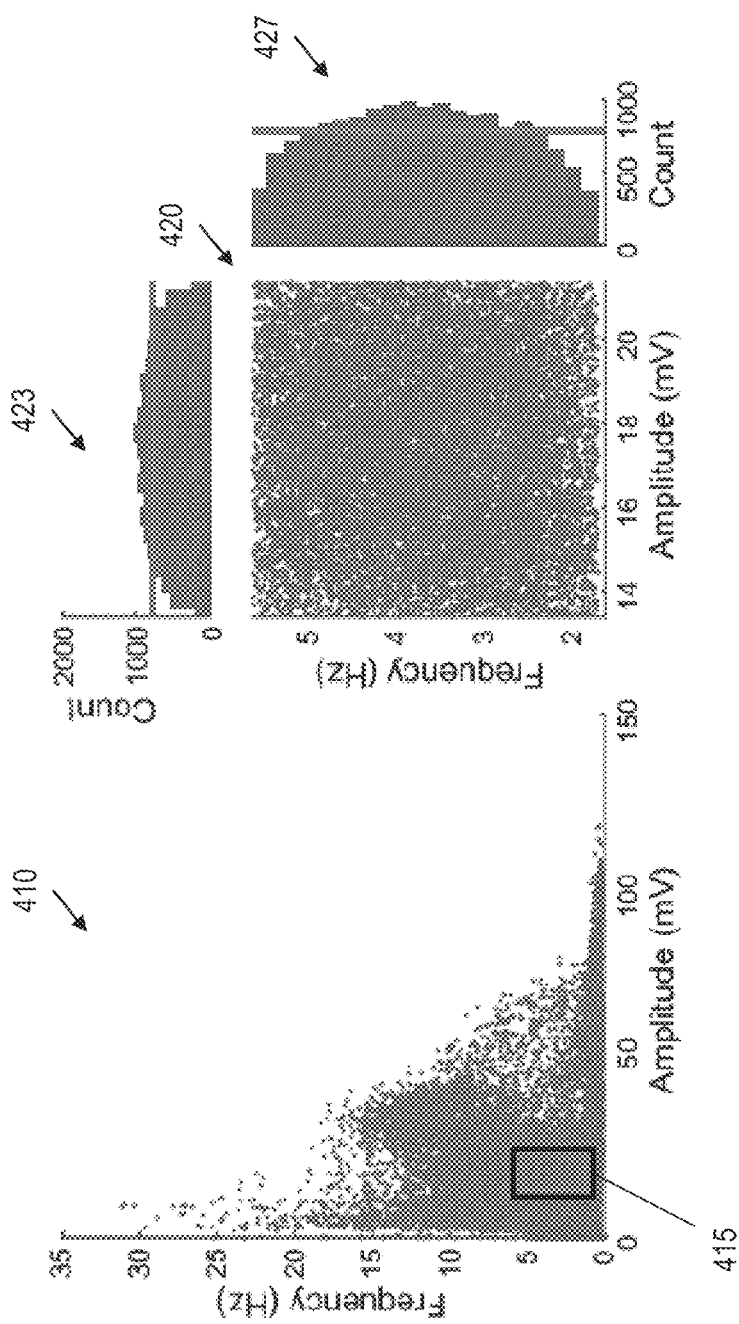
FIG. 4 depicts example plots for a pair of traits targeted during such a parameter search according to one or more embodiments of the present invention.

FIG. 4 depicts example plots for a pair of traits targeted during such a parameter search according to one or more embodiments of the present invention. In the depicted example scenario, the traits that are searched for are oscillation amplitude and frequency of substantia nigra pars compacta dopamine neuron. In a scatter plot 410 ion channels with different values of the two traits are plotted from the ion channel database (corresponding to block 310). The rectangle 415 depicts the ion channels that can meet the search criteria, for example, ion channels that generate neuron traits such as oscillation amplitude and frequency that represent the 'healthy' range in which error values are zero and selection is driven by the crowdedness penalty. Further, scatter plot 420 depicts the ion channels that are searched and selected from within the ion channels depicted by the rectangle 415. In this example the crowdedness penalty has biased the evolution such that the current generation contains models that lead to new models being generated approximately uniformly in this trait-space, as indicated by the histograms 423 and 427. It should be noted that the plots in FIG. 4 are exemplary, and that in other examples, different plots can be generated, and further different trait values, different measurement ranges can be used.

Referring back to the flowchart, the method further includes analyzing the neuronal models, such as by using PLSR, to identify components, that is parameters of the neuronal model that affect the traits that are being analyzed for the patient, at 340. The analysis identifies components capable of transforming patient phenotypes to desired "healthy" states and their coefficients over ion channel parameters ranked according to contributions of each component on the trait. For example, Extracellular K+, Na+, and Ca2+ ions can all influence the resting membrane potential of the neuron; further, NALCN, in association with UNC79 and UNC80, contributes a basal Na+ leak conductance in neurons. Thus, a combination of one or more ion channels can contribute to a particular trait. The analysis performed identifies the parameters that affect the "healthy" measurements as identified by the subpopulation of ion channels (rectangle 415).

Figure 5:
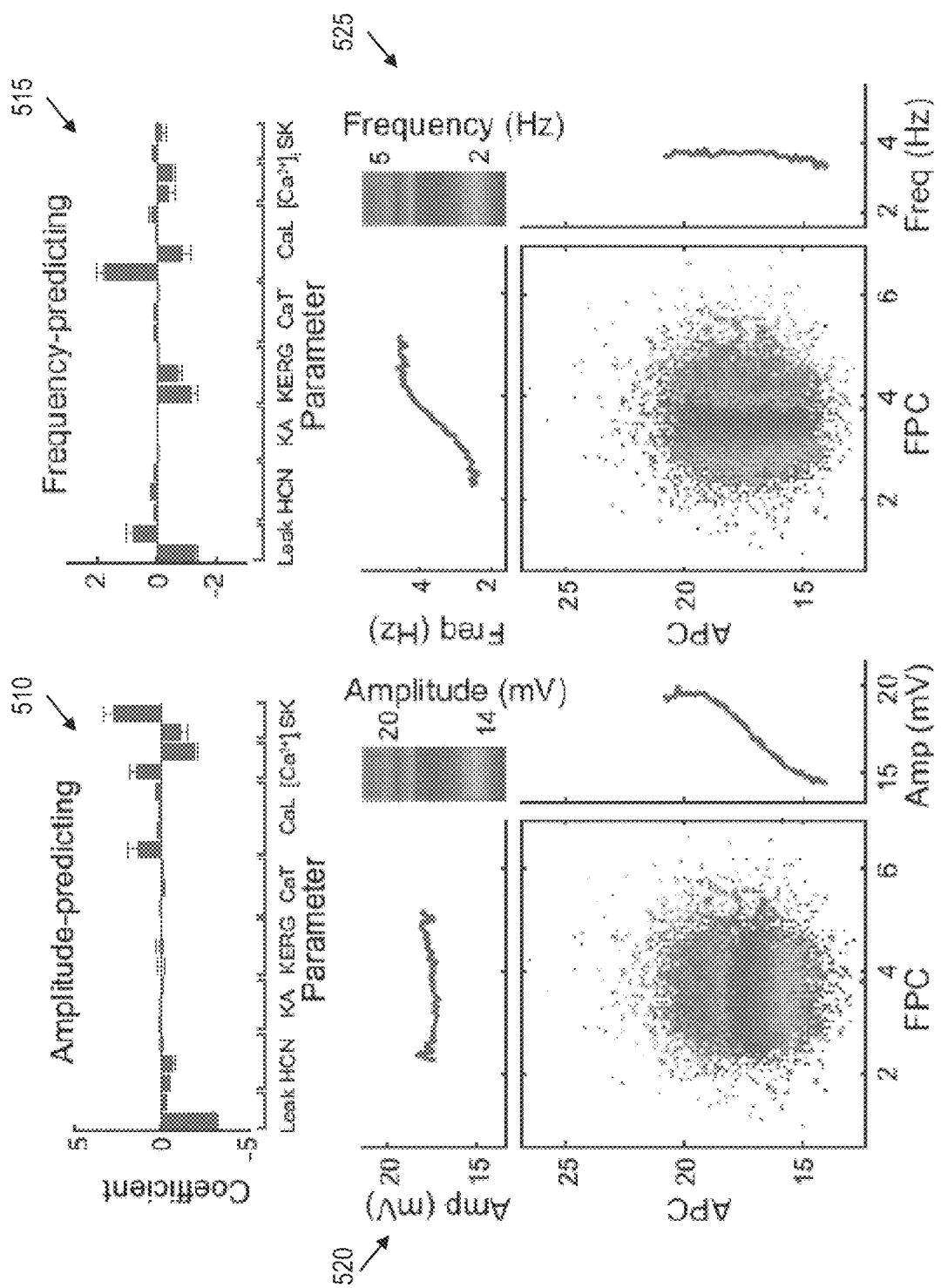
FIG. 5 depicts example plots illustrating results of a PLSR performed on neuronal models represented in FIG. 4 according to one or more embodiments of the present invention.

FIG. 5 depicts example plots illustrating results of a PLSR performed on neuronal models represented in FIG. 4 according to one or more embodiments of the present invention. All parameter sets producing a "healthy" combination of traits are regressed against their trait values. This provides a set of coefficients for each trait that show how deviations in parameter space are predicted to affect the trait. The plots 510 and 515 show example coefficient vectors for the amplitude and frequency traits shown in FIG. 4. These coefficient vectors represent a prediction about the precise combination of intracellular parameters in the real neurons that should be modulated by a therapeutic to control the traits of frequency and amplitude. Further, plots 520 and 525 show the predicted trait values calculated by multiplying the normalized parameter values of each neuronal model by either the amplitude or frequency for predicting components shown in the top part of the figure. Both plots show the same set of models, but the predicted trait values are orthogonal, indicating that independent control of these two traits is possible, and a drug could be targeted at one or the other set of a parameter coefficients responsible for controlling one of the other trait independently.

Referring back to the flowchart, the method further includes ranking and grouping the one or more drugs to be selected for the patient based on their ability to target the complete set of coefficients that are identified by the analysis, at 350. The method further includes outputting the ranked list of drugs, at 360. The output can also include the grouping of the drugs, where the grouping provides a combination of drugs that together affect the parameters, and in turn the traits.

In one or more examples, selecting the drug for the patient based at least in part on the identified coefficients includes accessing a drug database to identify drugs that alter the ion channels associated with the identified components. For example, if the identified coefficients are for voltage-gated sodium (Nav 1) channels, which play a key role in the origination and propagation of sensory nerve action potentials necessary for pain signaling, identified drugs can include local applications of nonsubtype-selective sodium channel blockers, such as novocaine, which provide complete pain relief through conduction block.

The present invention accordingly facilitates utilization of genotypic information to parameterize simulations, allowing a prediction of the effect of different perturbations on the individual. The present invention further facilitates establishing a set of intracellular parameter limits from the allelic information. Further, the present invention facilitates a drug/dosage selection process that does not directly rely on the established phenotype, but instead on the simulations targeting the electrophysiological trait values that represent the desired effect of the drug. In one or more embodiments of the present invention regression is used to derive the elements of the neuronal system that should be modified by a drug to control a feature of the behavior of that system representative of a patient.

In other words, the present invention facilitates exposure of a simulation to a particular test compound, selected in advance as a candidate therapeutic for modifying traits in a specific tissue, such as in the brain. The simulation predicts the efficacy of the drug at altering the fractional occupancy of receptors that the drug might affect in that tissue. The embodiments of the present invention thus facilitate predicting suitable targets for the drugs in terms of elements of the simulated system that can be modulated to produce robust trait modifications.

The present invention facilitates computer generation of neuronal models by first modeling the phenotype of an individual using a mechanistic simulation constrained by the genotype, and then performing an automated parameter sensitivity analysis to establish a recovery vector in parameter space to transition the neuronal model from disease to healthy state, which can be used to select a drug or a combination 'cocktail' of drugs through another method that compares known drug targets with the recovery vector.

It should be noted that the present invention is not specific to any particular neurophysiological model. A model of sub stantia nigra dopamine neurons is used in the figures (FIGS. 4 and 5) by way of an example, however, the present invention can be similarly applied to any dopamine neuron models, as well as previously published models of any neuron types from any brain regions that are implicated in neurophysiological dysfunction. The specific neurophysiological model used depends on the question and problem that is intended to be addressed by the pharmaceutical. Further, the neuronal models that are generated can include multiple ion channels, for example 10 ion channels, 15 ion channels, and thousands and millions of such neuronal models are analyzed to identify the drug dosage combination for the patient. Thus, the system described herein analyzes large amounts of data in an efficient manner providing an improvement to computer technology, particularly personalized drug identification systems.

The one or more embodiments of the present invention include a method for selecting a drug combination that includes at least one dose of at least one drug with known physiological target based on a prediction of a clinically beneficial phenotypic change. The method includes enumerating the changes in parameters of a physiological component model to represent the drug-target combination. Further, the method includes providing inputs from the physiological component model to a simulation of a neuron cell model and receiving at least one additional physiological component model input. Further, the method includes generating models producing a range of observed phenotypes from multiple simulations of the neuron cell model controlled by a population-based evolutionary search algorithm varying the physiological component models' parameters. The method further includes analyzing the combined effects of parameter changes to the at least two physiological component models on the neuron cell model by identifying coefficients of parameter change components using partial least squares regression of model parameter sets to the clinically beneficial phenotypic changes. Other algorithms can also be used for the identification of the coefficients. The method further includes selecting the drug combination based on maximizing the vector projection of an expected drug-target change in parameters of the at least two physiological component models onto the coefficients of parameter changes most correlated with the beneficial phenotypic change.

Further, one or more embodiments of the present invention includes a system for selecting a drug combination including at least one dose of at least one drug with known physiological target based on a prediction of a clinically beneficial phenotypic change. The system includes a searchable database of changes in parameters of a physiological component model to represent the drug-target combination. The system also includes a simulation software for simulating the physiological component model and providing inputs from the model and at least one additional physiological component model to a neuron cell model. Further, the system includes a simulation hardware for calculating models repeatedly to produce a range of observed phenotypes from multiple simulations of the neuron cell model controlled by a population-based evolutionary search algorithm varying the physiological component models' parameters. Further, an analysis software in the system identifies the combined effects of parameter changes to the at least two physiological component models on the neuron cell model by identifying coefficients of parameter change components using partial least squares regression of model parameter sets to the clinically beneficial phenotypic changes. Further, the system includes a ranking hardware for calculating the partial least squared regression, scoring the vector projection of an expected drug-target change in parameters of the at least two physiological component models onto the coefficients of parameter changes most correlated with the beneficial phenotypic change, and ranking drug-target combinations based on score.

In one or more examples, the neuron cell model contributes inputs to a neural tissue simulation and a measure of the neural tissue simulation corresponds to the range of observed phenotypes and the beneficial clinical change. Alternatively, or in addition, in one or more examples, the neuron cell model contributes inputs to a brain model simulation and a measure of the brain model simulation corresponds to the range of observed phenotypes and the beneficial clinical change.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are to be construed in the broadest sense, superseding any other implied definitions hereinbefore or hereinafter unless expressly asserted to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

It will also be appreciated that any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Such computer storage media may be part of the device or accessible or connectable thereto. Any application or module herein described may be implemented using computer readable/executable instructions that may be stored or otherwise held by such computer readable media.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for generating neuronal models for personalized drug treatment selection for a patient to treat a neurophysiological trait, the method comprising:

receiving allelic information for at least one neurophysiological coding region of a genome of the patient;

receiving a physiological model of disease associated with a phenotype of the patient;

determining, from an ion channel database, a set of ion channels correlated with the allelic information;

receiving a set of physiological measurement ranges, each physiological measurement range associated with a corresponding ion channel from the determined set of ion channels;

performing, by a neuron model simulator executed by a processor, a simulation to generate multiple neuronal models comprising the set of ion channels with parameter values within the corresponding physiological measurement ranges, wherein the simulation to generate the multiple neuronal models uses an optimization comprising at least in part a soft thresholding of error values and a penalty term for crowdedness;

modulating, by the neuron model simulator executed by the processor, the set of ion channels simultaneously along axes of control, thereby providing control over the trait;

determining, by the neuron model simulator executed by the processor, components that affect the physiological model of disease by analyzing the generated neuronal models; and selecting, by the processor, a drug for the patient based at least in part on the determined components having been determined by the neuron model simulator, such that the selected drug is a targeted and a treatment for the neurophysiological trait of the patient.

2. The computer-implemented method of claim 1, wherein the set of physiological measurement ranges comprises ranges that correspond to neuronal models that generate healthy neuronal responses.

3. The computer-implemented method of claim 2, wherein the set of physiological measurement ranges further comprises ranges that correspond to neuronal models that generate diseased neuronal responses.

4. The computer-implemented method of claim 1, wherein analyzing the generated neuronal models comprises performing a partial least square regression using the ion channel parameter values of the generated neuronal models and the physiological model.

5. The computer-implemented method of claim 1, wherein the penalty term for crowdedness biases the simulation toward less crowded regions of a trait-space.

6. The computer-implemented method of claim 1, wherein the physiological model of disease comprises at least two trait values.

7. The computer-implemented method of claim 6, wherein selecting the drug for the patient based at least in part on the determined components comprises accessing a drug database to identify drugs with ion channel alterations associated with the determined components.

8. A computer system for generating neuronal models for personalized drug treatment selection for a patient to treat a neurophysiological trait, the system comprising:

a memory; and a processor communicatively coupled to the memory, the processor configured to:

receive allelic information for at least one neurophysiological coding region of a genome of the patient;

receive a physiological model of disease associated with a phenotype of the patient;

determine, from an ion channel database, a set of ion channels correlated with the allelic information;

receive a set of physiological measurement ranges, each physiological measurement range associated with a corresponding ion channel from the determined set of ion channels;

perform, by a neuron model simulator executed by the processor, a simulation to generate multiple neuronal models comprising the set of ion channels with parameter values within the corresponding physiological measurement ranges, wherein the simulation to generate the multiple neuronal models uses an optimization comprising at least in part a soft thresholding of error values and a penalty term for crowdedness;

modulate, by the neuron model simulator executed by the processor, the set of ion channels simultaneously along axes of control, thereby providing control over the trait;

determine, by the neuron model simulator executed by the processor, components that affect the physiological model of disease by analyzing the generated neuronal models; and select, by the processor, a drug for the patient based at least in part on the determined components having been determined by the neuron model simulator, such that the selected drug is a targeted and a treatment for neurophysiological the trait of the patient.

9. The system of claim 8, wherein the set of physiological measurement ranges comprises a first set of ranges that correspond to neuronal models that generate healthy neuronal responses, and a second set of ranges that correspond to neuronal models that generate diseased neuronal responses.

10. The system of claim 8, wherein analyzing the generated neuronal models comprises performing a partial least square regression using the ion channel parameter values of the generated neuronal models and the physiological model.

11. The system of claim 9, wherein analyzing the generated neuronal models comprises using a 2-gate hyperplane normal algorithm to determine a hyperplane between a first set of neuronal models corresponding to the first set of ranges and a second set of neuronal models corresponding to the second set of ranges.

12. The system of claim 8, wherein the penalty term for crowdedness biases the simulation toward less crowded regions of a trait-space.

13. The system of claim 8, wherein the physiological model of disease comprises at least two trait values.

14. The system of claim 13, wherein selecting the drug for the patient based at least in part on the determined components comprises accessing a drug database to identify drugs with ion channel alterations associated with the determined components.

15. A computer program product comprising a computer storage device having computer readable instructions stored therein, the computer readable instructions are executable by a processing unit for generating neuronal models for personalized drug treatment selection for a patient to treat a neurophysiological trait, the selection comprising:

receiving allelic information for at least one neurophysiological coding region of a genome of the patient;

receiving a physiological model of disease associated with a phenotype of the patient;

determining, from an ion channel database, a set of ion channels correlated with the allelic information;

receiving a set of physiological measurement ranges, each physiological measurement range associated with a corresponding ion channel from the determined set of ion channels;

performing, by a neuron model simulator executed by the processing unit, a simulation to generate multiple neuronal models comprising the set of ion channels with parameter values within the corresponding physiological measurement ranges, wherein the simulation to generate the multiple neuronal models uses an optimization comprising at least in part a soft thresholding of error values and a penalty term for crowdedness;

modulating, by the neuron model simulator executed by the processor, the set of ion channels simultaneously along axes of control, thereby providing control over the trait;

determining, by the neuron model simulator executed by the processor, components that affect the physiological model of disease by analyzing the generated neuronal models; and selecting, by the processor, a drug for the patient based at least in part on the determined components having been determined by the neuron model simulator, such that the selected drug is a targeted and a treatment for the neurophysiological trait of the patient.

16. The computer program product of claim 15, wherein the set of physiological measurement ranges comprises a first set of ranges that represent neuronal models that generate healthy neuronal responses, and a second set of ranges that represent neuronal models that generate diseased neuronal responses.

17. The computer program product of claim 15, wherein analyzing the generated neuronal models comprises performing a partial least square regression using the ion channel parameter values of the generated neuronal models and the physiological model of disease.

18. The computer program product of claim 16, wherein analyzing the generated neuronal models comprises using a 2-gate hyperplane normal algorithm to determine a hyperplane between a first set of neuronal models corresponding to the first set of ranges and a second set of neuronal models corresponding to the second set of ranges.

19. The computer program product of claim 15, wherein the penalty term for crowdedness biases the simulation toward less crowded regions of a trait-space.

20. The computer program product of claim 15, wherein the physiological model comprises at least two trait values, and wherein selecting the drug for the patient based at least in part on the determined components comprises accessing a drug database to identify drugs with ion channel alterations associated with the determined components.

* * * * *